United States Patent
Navia et al.

(10) Patent No.: US 7,591,847 B2
(45) Date of Patent: Sep. 22, 2009

(54) STENTLESS BIOPROSTHETIC VALVE HAVING CHORDAE FOR REPLACING A MITRAL VALVE

(75) Inventors: Jose' Luis Navia, Shaker Hts., OH (US);
Jose' A. Navia, Buenos Aires (AR);
Jorge L. Jordana, Buenos Aires (AR)

(73) Assignee: The Cleveland Clinic Foundation, Cleveland, OH (US)

( * ) Notice: Subject to any disclaimer, the term of this patent is extended or adjusted under 35 U.S.C. 154(b) by 1095 days.

(21) Appl. No.: 10/683,341

(22) Filed: Oct. 10, 2003

(65) Prior Publication Data
US 2004/0122513 A1 Jun. 24, 2004

Related U.S. Application Data

(60) Provisional application No. 60/417,912, filed on Oct. 10, 2002.

(51) Int. Cl.
*A61F 2/24* (2006.01)
(52) U.S. Cl. ........................... 623/2.1; 623/2.13
(58) Field of Classification Search ............... 623/1.24, 623/1.26, 2.1, 2.12, 2.13, 2.38, 2.42, 904, 623/2.36, 2.37, 2.41
See application file for complete search history.

(56) References Cited

U.S. PATENT DOCUMENTS

| 4,790,844 A | 12/1988 | Ovil |
| 4,960,424 A | 10/1990 | Grooters ............... 128/898 |
| 5,156,621 A | 10/1992 | Navia et al. |
| 5,163,954 A | 11/1992 | Curcio et al. ........... 623/2.41 |
| 5,415,667 A | 5/1995 | Frater ..................... 623/2.11 |
| 5,500,015 A | 3/1996 | Deac |
| 5,554,184 A | 9/1996 | Machiraju |

(Continued)

FOREIGN PATENT DOCUMENTS

WO    WO 9640007 A1 * 12/1996

(Continued)

OTHER PUBLICATIONS

"Functional Evaluation of the Medtronic Stentless Porcine Xenograft Mitral Valve in Sheep", Paul Dagum, MD, PhD, et al.; Circulation. 1999; 100[suppl II]:II-70-II-77.

(Continued)

*Primary Examiner*—Brian E. Pellegrino
(74) *Attorney, Agent, or Firm*—Tarolli, Sundheim, Covell & Tummino LLP (57) ABSTRACT

A stentless bioprosthetic valve includes at least one piece of biocompatible material comprising a bi-leaflet conduit having a proximal end and a distal end. The proximal end defines a first annulus for suturing to the valve annulus. The conduit includes first and second leaflets that mimic the native leaflets and extend between the conduit ends. The distal end defines a second annulus at which the first and second leaflets terminate. The conduit further includes first and second pairs of prosthetic chordae projecting from the leaflets at the second annulus. One of the first pair of prosthetic chordae extends from the first leaflet and has a distal end for suturing to a papillary muscle and the other of the first pair of prosthetic chordae extends from the first leaflet and has a distal end for suturing to another papillary muscles.

11 Claims, 5 Drawing Sheets

U.S. PATENT DOCUMENTS

| | | |
|---|---|---|
| 5,733,331 A | 3/1998 | Peredo |
| 5,824,067 A | 10/1998 | Gross |
| 5,928,281 A * | 7/1999 | Huynh et al. ............... 623/2.14 |
| 6,074,417 A | 6/2000 | Peredo |
| 6,312,464 B1 | 11/2001 | Navia |
| 6,358,277 B1 | 3/2002 | Duran |
| 6,409,759 B1 | 6/2002 | Peredo |
| 2002/0052651 A1 | 5/2002 | Myers et al. |
| 2002/0091441 A1 | 7/2002 | Guzik ....................... 623/2.13 |
| 2003/0069635 A1 | 4/2003 | Carledge et al. |

FOREIGN PATENT DOCUMENTS

WO    WO-01/54624 A1    8/2001

OTHER PUBLICATIONS

New U.S. Navia et al. patent application for Method and Apparatus for Replacing a Mitral Valve With a Stentless Bioprosthetic Valve, filed Oct. 10, 2003.

* cited by examiner

STENTLESS BIOPROSTHETIC VALVE HAVING CHORDAE FOR REPLACING A MITRAL VALVE

RELATED APPLICATION

This application claims priority from U.S. provisional patent application Ser. No. 60/417,912, filed on Oct. 10, 2002, the subject matter of which is incorporated herein by reference.

TECHNICAL FIELD

The present invention relates to a method and apparatus for replacing a native mitral valve with a stentless bioprosthetic valve having prosthetic chordae.

BACKGROUND OF THE INVENTION

The mitral valve is a functional unit composed of multiple dynamically interrelated units. During cardiac cycle, the fibrous skeleton, the anterior and posterior leaflets, the papillary muscles, the chordae tendinea, and the ventricular and atrial walls all interplay symphonically to render a competent valve. The complex interaction between the mitral valve and the ventricle by the subvalvular apparatus (the papillary muscles and the chordae tendinea) is essential in that it maintains the continuity between the atrio-ventricular ring (which is part of the fibrous skeleton of the heart) and the ventricular muscle mass, which is essential for the normal function of the mitral valve.

The chordae tendinea, which connect the valve leaflets to the papillary muscles (PM) act like "tie rods" in an engineering sense. Not only do the chordae tendinea prevent prolapse of the mitral valve leaflets during systole, but they also support the left ventricular muscle mass throughout the cardiac cycle.

To function adequately, the mitral valve needs to open to a large orifice area and, for closure, the mitral leaflets need to have an excess of surface area (i.e. more than needed to effectively close the mitral orifice). On the other hand, systolic contraction of the posterior ventricular wall around the mitral annulus (MA) creates a mobil D-shaped structure with sphincter-like function which reduces its area by approximately 25% during systole, thus exposing less of the mitral leaflets to the stress of the left ventricular pressure and flow.

Although the primary function of the mitral valve is to act as a one-way no return valve, it has been postulated that the structural integrity of the MA-PM continuity is essential for normal left ventricular function.

Since it was first suggested in the mid-1960's that preservation of the subvalvular apparatus during mitral valve replacement might prevent low cardiac output in the early postoperative period, this important observation was largely overlooked by most surgeons for many years.

There is now considerable laboratory and clinical evidence to corroborate this position, as evidence has demonstrated that chordal excision is associated with a change in left ventricular shape from oval to spherical, which can lead to a significant increase in postoperative left ventricular end systolic volume and wall stress, along with a decline in ejection fraction.

The majority of evidence appears to support the concept that preservation of the subvalvular apparatus with the MA-PM continuity in any procedure on the mitral valve is important for the improved long-term quality and quantity of life after mitral valve surgery. Reparative techniques to correct mitral valve disease are often the best surgical approach for dealing with mitral valve abnormalities, however mitral valvuloplasty is not always feasible because of extensive fibrosis, leaflets calcification, or massive chordal rupture. Mitral valve replacement using either a mechanical valve or a bioprosthetic valve thus remains the best surgical solution for severe mitral valve disease.

However, there are many additional problems that face patients after valve replacement with a prosthetic valve. Valve-related problems include limitation of the mitral flow (due to a small effective orifice area) during exercise and high cardiac output imposed by a smaller size artificial valve as compared with the natural valve orifice area.

Further, the rigid structure of an artificial valve prevents the physiologic contraction of the posterior wall of the left ventricle surrounding the MA during systole. Surgical interruption of the MA-PM continuity accounts for changes in geometry mechanics and performance of the left ventricle. Myocardial rupture, a lethal complication of mitral valve replacement, results from excision or stretching of the papillary muscle in a thin and fragile left ventricle. Myocardial rupture can also be caused by a strut of a stented bioprosthetic valve eroding into or protruding through the posterior left ventricle wall. Maintaining the MA-PM continuity appears to provide a substantial degree of protection from this devastating complication. Also, the difficulties in controlling adequate anticoagulation for a mechanical valve bring a high morbidity risk factor of thromboembolic and hemorragic complication and endocarditis.

Stented tissue valves, although less thrombogenic, are not reliably durable and, because of the rigid stent, they are less hemodynamically efficient. Stentless valves are considered to have the potential advantages of superior hemodynamic performance and enhanced durability and have already showed satisfactory mid-term results in the aortic position. From these points of view, it is expected that new stentless valves in the mitral position will be developed. However, stentless mitral valves are not yet commonly available for clinical use because of the anatomical and functional complexity of the mitral valve and the subvalvular apparatus, resulting in the difficulties of the design and implantation procedures of the stentless mitral valves. The present invention provides and apparatus and method for replacing a native mitral valve with a stentless, bioprosthetic valve that maintains the anatomical and functional complexity of the mitral valve and the subvalvular apparatus.

SUMMARY OF THE INVENTION

The present invention is a stentless bioprosthetic valve for replacing a native mitral valve resected from a valve annulus in a heart. The native mitral valve has anterior and posterior leaflets and associated native chordae tendinea. The bioprosthetic valve comprises at least one piece of biocompatible material comprising a bi-leaflet conduit having dimensions that correspond to the dimensions of the native mitral valve. The conduit has a proximal end and a distal end. The proximal end of the conduit defines a first annulus for suturing to the valve annulus in the heart. The conduit includes first and second leaflets that mimic the three-dimensional anatomical shape of the anterior and posterior leaflets of the native mitral valve. The first and second leaflets extend between the proximal end and the distal end of the conduit. The distal end of the conduit defines a second annulus at which the first and second leaflets terminate. The conduit further includes first and second pairs of prosthetic chordae projecting from the first and second leaflets at the second annulus. Each of the prosthetic chordae comprises a solid uninterrupted extension of the at least one piece of biocompatible material. The first and second pairs of prosthetic chordae provide prolapse prevention for the bioprosthetic valve and support the left ventricular muscle throughout the cardiac cycle. One of the first pair of prosthetic chordae extends from the first leaflet and has a distal end for suturing to one of the two papillary muscles and the other of the first pair of prosthetic chordae extends from the first leaflet and has a distal end for suturing to the other of the two papillary muscles. One of the second pair of prosthetic chordae extends from the second leaflet and has a distal end for suturing to one of the two papillary muscles and the other of the second pair of prosthetic chordae extends from the second leaflet and has a distal end for suturing to the other of the two papillary muscles.

In accordance with one aspect of the invention, the at least one piece of biocompatible material comprises harvested biological tissue.

In accordance with another aspect of the invention, the harvested biological tissue comprises pericardial tissue.

In accordance with yet another aspect of the invention, the at least one piece of biocompatible material comprises an artificial tissue.

In accordance with another feature of the invention, the bioprosthetic valve further comprises a biocompatible, unstented ring connected to the first annulus for supporting the first annulus and for suturing to the valve annulus of the heart. The ring, when sutured to the valve annulus, impedes dilatation of the valve annulus and preserves motion of the valve annulus.

The present invention also provides a method for replacing a native mitral valve having anterior and posterior leaflets with a stentless bioprosthetic valve. According to the inventive method, at least one piece of biocompatible material that comprises a bi-leaflet conduit having dimensions that correspond to the dimensions of the native mitral valve being replaced is provided. The conduit has a proximal end and a distal end. The proximal end defines a first annulus and the distal end defines a second annulus. The conduit further includes first and second leaflets that mimic the three-dimensional shape of the anterior and posterior leaflets of the native mitral valve. The first and second leaflets extend from the proximal end and terminate at the distal end of the conduit. The conduit further includes first and second pairs of prosthetic chordae projecting from the first and second leaflets at the second annulus. Each of the prosthetic chordae comprises a solid uninterrupted extension of the at least one piece of biocompatible material. The entire native mitral valve is resected from the valve annulus. A distal end of one of the first pair of prosthetic chordae that extends from the first leaflet is sutured to one of the two papillary muscles. A distal end of the other of the first pair of prosthetic chordae that extends from the first leaflet is sutured to the other of the two papillary muscles. A distal end of one of the second pair of prosthetic chordae that extends from the second leaflet is sutured to one of the two papillary muscles. A distal end of the other of the second pair of prosthetic chordae that extends from the second leaflet is sutured to the other of the two papillary muscles. The first annulus of the conduit is sutured to the valve annulus of the native mitral valve to secure the bioprosthetic valve to the valve annulus. The first and second pairs of prosthetic chordae provide prolapse prevention and left ventricular muscle support functions for the bioprosthetic valve and assist the bioprosthetic valve in maintaining the continuity between the valve annulus and the papillary muscles.

In accordance with another aspect of the inventive method, a biocompatible, unstented support ring encircles the first annulus. The support ring is sutured to the valve annulus of the heart to secure the bioprosthetic valve to the valve annulus and to impede dilatation of the valve annulus and preserve motion of the valve annulus.

BRIEF DESCRIPTION OF THE DRAWINGS

The foregoing and other features of the present invention will become apparent to those skilled in the art to which the present invention relates upon reading the following description with reference to the accompanying drawings, in which.

DESCRIPTION OF EMBODIMENTS

Figures 4, 5:
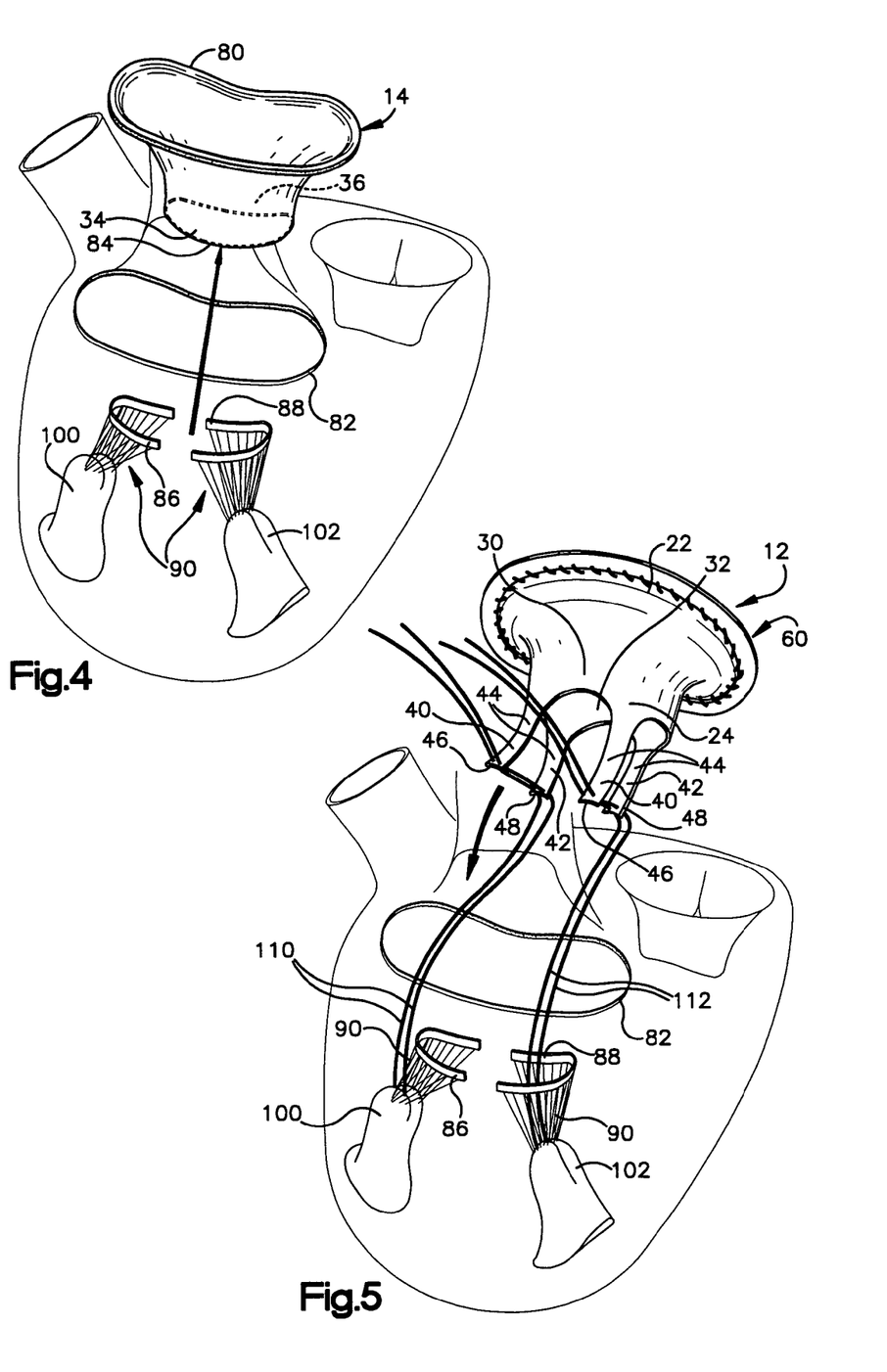
FIG. 4 is a perspective view of the left ventricle illustrating the native mitral valve being resected in accordance with the present invention.
FIG. 5 is a perspective view of the valve of FIG. 1 showing the valve at an initial stage of implantation in the native mitral annulus shown in FIG. 4.

The present invention relates to a method and apparatus for replacing a native mitral valve with a stentless bioprosthetic valve having prosthetic chordae. As representative of the present invention, FIG. 1 illustrates an apparatus 10 comprising a stentless bioprosthetic valve 12 for replacing a native mitral valve 14 (FIG. 4).

Figure 1:
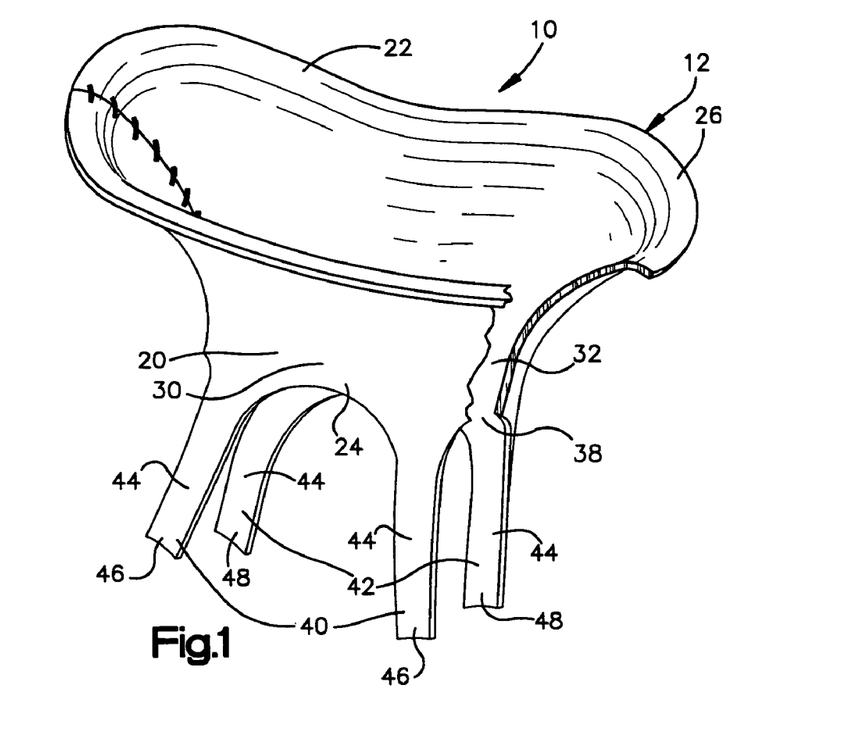
FIG. 1 is a perspective view of a stentless bioprosthetic valve having prosthetic chordae.
Figure 2:
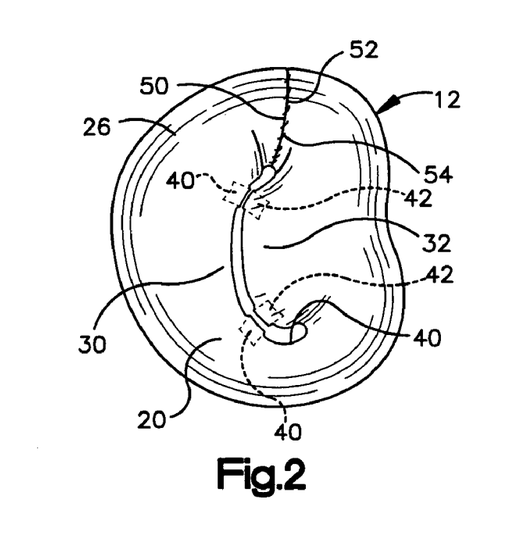
FIG. 2 is a plan view of the valve of FIG. 1 showing the valve in a closed position.

The bioprosthetic valve 12 shown in FIGS. 1 and 2 is made from one or more pieces of biocompatible material formed into a bi-leaflet conduit 20 having dimensions that correspond to the dimensions of the native mitral valve 14. The conduit 20 has a proximal end 22 and a distal end 24. The proximal end 22 defines a first annulus 26 for suturing to the valve annulus of the native mitral valve 14, as described further below.

The conduit 20 further includes first and second leaflets 30 and 32 that mimic the three-dimensional anatomical shape of the anterior and posterior leaflets 34 and 36 (FIG. 4), respectively, of the native mitral valve 14. The first and second leaflets 30 and 32 extend between the proximal end 22 and the distal end 24 of the conduit 20. The distal end 24 of the conduit 20 defines a second annulus 38 at which the first and second leaflets 30 and 32 terminate.

The conduit 20 further includes first and second pairs 40 and 42, respectively, of prosthetic chordae 44 that project from the first and second leaflets 30 and 32 at the second annulus 38. Each of the prosthetic chordae 44 comprises a solid uninterrupted extension of the at least one piece of biocompatible material. Each of the first pair 40 of prosthetic chordae 44 has a distal end 46 and each of the second pair 42 of prosthetic chordae has a distal end 48.

The biocompatible material of the bioprosthetic valve 12 may be a harvested biological material including, but not limited to, bovine pericardial tissue, horse pericardial tissue, or porcine pericardial tissue. The biocompatible material may also be suitable synthetic material including, but not limited to, polyurethane or expanded PTFE.

In the case of, for example, bovine pericardial tissue, the tissue is harvested in slaughterhouses and kept in cold saline solution for transport to minimize the effects of autolysis and bacterial/enzymatic reactions on the tissue. The pericardial tissue is dissected to be clean of all fatty and other biological materials. The pericardial material is then formed into a tri-dimensional shape of what will be the leaflet structure of the bioprosthetic valve 12 by attaching the pericardial tissue to a mold (not shown) having such a shape. The pericardial material is also trimmed to roughly form the four prosthetic chordae 44 that extend from the distal end 24 of the conduit 20.

Figure 2A:
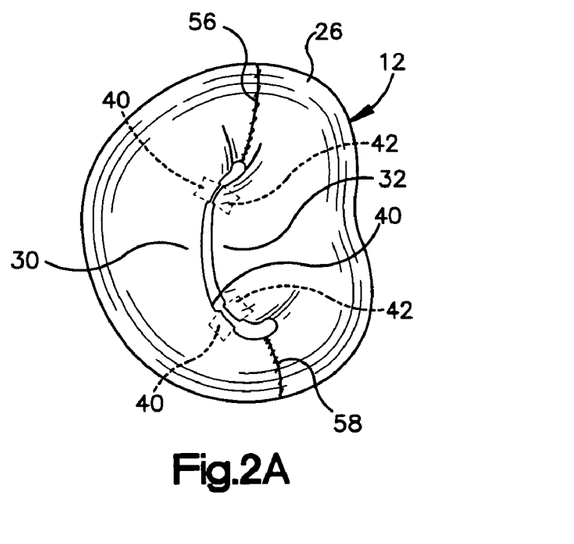
FIG. 2A is view similar to FIG. 2 illustrating an alternate construction for the valve.

The molds are produced in different sizes to render valves of different sizes to match the needs of the different patients (i.e., sizes between 23 and 35 mm in diameter). The molds can have either a male shape of what will be the inflow aspect of the valve 12, or a female aspect of the same. The pericardial tissue is applied to the molds and accommodated to ensure the complete conformability to the mold's shape. The bioprosthetic valve 12 can be made with only one piece of pericardial tissue, as shown in FIGS. 1 and 2. Alternatively, the bioprosthetic valve 12 can be made with two pieces of pericardial tissue, one of which will form the first leaflet 30 and the other forms the second leaflet 32 of the prosthetic valve, as may be seen in FIG. 2A.

Once the pericardial piece(s) is fully conformed on the mold, the biological material is tanned by immersion in an adequate fixation solution (e.g. 0.65% glutaraldehyde solution buffered at pH 7.4). This tanning can be achieved with an ample range of glutaraldehyde concentrations (e.g. between 0.4% and 5%).

When the pericardial tissue is already fixed with the fixation agent, it is then separated from the mold and the lateral edges 50 and 52 (FIG. 2) are sutured together along a seam 54 to form the tubular conduit 20. In the alternate embodiment of FIG. 2A where two pieces of pericardial tissue are used, it is necessary to suture the tissue in two locations, thereby forming two seams 56 and 58. The seams 54, 56, and 58 are always placed at what will be the commissures of the prosthetic valve 12, where the first leaflet 30 meets the second leaflet 32.

Figures 3, 3A:
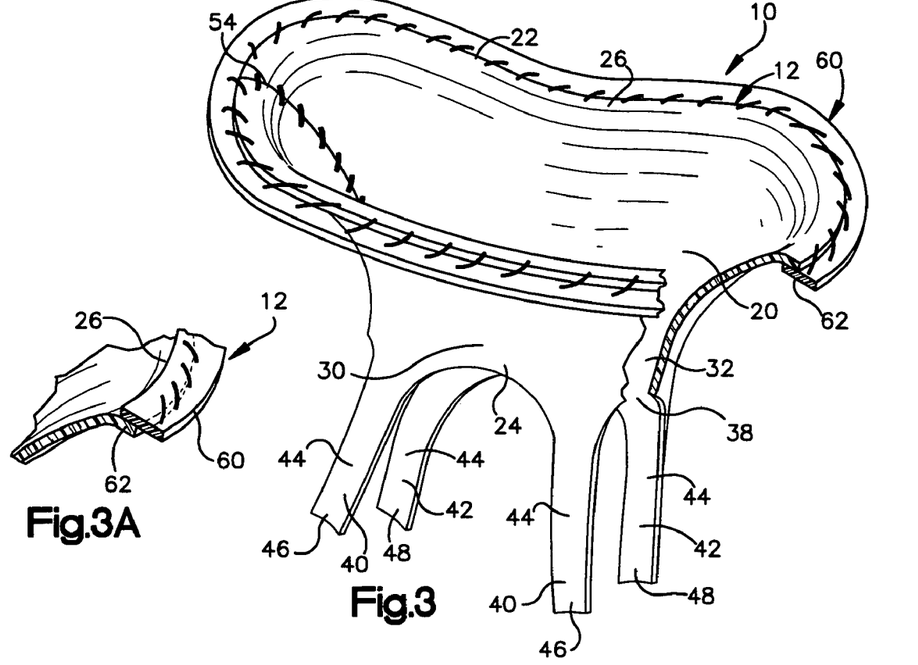
FIG. 3 is a perspective view, partially in section, of the valve of FIG. 1 and illustrating a method for forming a ring at the proximal end of the valve.
FIG. 3A is a view of a portion of FIG. 3 showing an alternate construction.

In accordance with one embodiment of the present invention, the valve 12 further includes a flexible, unstented, biocompatible ring 60 (FIG. 3) that is sutured about the first annulus 26 along a proximal edge 62 at the proximal end 22 of the conduit 20. The ring 60 is for supporting the first annulus 26 and for suturing the valve 12 to the valve annulus in the heart. The ring 60 may be made from a biological material such as, for example, bovine or porcine pericardial tissue, or from a suitable synthetic material, such as the material marketed under the tradename DACRON or the material marketed under the tradename TEFLON. In the embodiment of FIG. 3, the ring 60 is positioned underneath the proximal edge 62 of the conduit 20. Alternatively, the ring 60 could be positioned on top of the proximal edge 62, as shown in FIG. 3A, or wrapped around the proximal edge, as shown in FIG. 3B, and subsequently sutured in place.

Figures 3B, 3C:
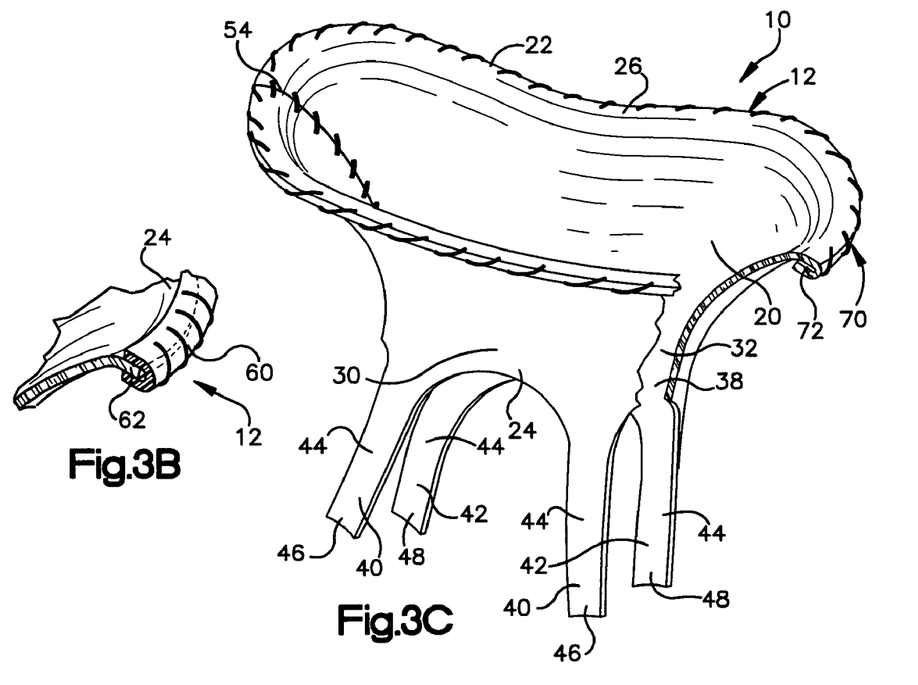
FIG. 3B is a view of a portion of FIG. 3 showing another alternate construction.
FIG. 3C is a perspective view, partially in section, of the valve of FIG. 1 and illustrating another method for forming a ring at the proximal end of the valve

According to an alternate construction for the valve 12 shown in FIG. 3C, a ring 70 is formed at the proximal end 22 of the conduit 20 by folding an additional portion 72 of the conduit 20 located at the proximal end 22 over onto itself and suturing the folded portion to the conduit.

Replacement of the native mitral valve 14 (FIG. 4) with the bioprosthetic valve 12 begins by taking either direct or echocardiographic measurements of the height of the anterior and posterior leaflets 34 and 36 of the native mitral valve. The size of the bioprosthetic valve 12 to be implanted is determined based on a measurement of the distance between the right and left trigones on the valve annulus. The distal ends 46 and 48 of the first and second pairs 40 and 42, respectively, of the prosthetic chordae 44 may be trimmed to adjust the height of the valve 12 based on the measurements taken. Four stay-sutures (6-0 silk) may be placed on the annulus of both mitral commissures and on the centers of the anterior and posterior leaflets 34 and 36 to help make sure that the bioprosthetic valve 12 is implanted in the proper anatomical orientation.

As may be seen in FIG. 4, the native mitral valve 14 is then dissected from the heart. The proximal end 80 of the native mitral valve 14 is resected from the valve annulus 82. At the distal end 84 of the native mitral valve 14, the anterior and posterior leaflets 34 and 36 are resected in such a manner that the free edges 86 and 88 of the anterior and posterior leaflets, respectively, remain intact and connected to the native chordae tendinea 90 which, in turn, remain attached to the papillary muscles 100 and 102. The native chordae tendinea 90 are left intact, at least temporarily, because they are helpful in handling the papillary muscles 100 during implantation of the valve 12.

Next, the prosthetic valve 12 is moved into the position shown in FIG. 5. The distal end 46 of the first pair 40 of prosthetic chordae 44 that extends from the first leaflet 30 is sutured to the papillary muscle 100. On the same commissural side of the valve 12, the distal end 48 of the second pair 42 of prosthetic chordae 44 that extends from the second leaflet 32 is also sutured to the papillary muscle 100. This suture, indicated by the reference number 110, may be a 4-0 Ethibond mattress suture with a pledget (not shown). The suture 110 extends through the distal ends 46 and 48 of both of the prosthetic chordae 44 and attaches to the papillary muscle 100 at a single location as shown in FIG. 5. Alternatively, the suture 110 may be threaded through one of the distal ends 46 and 48 of the prosthetic chordae 44 to attach it to the papillary muscle 100 at one location, and then threaded through the distal end of the other prosthetic chordae to attach it to the papillary muscle 100 at another location. It is further contemplated that a separate suture 110 could be used to attach each of the distal ends 46 and 48 of the prosthetic chordae to the papillary muscle 100.

The same procedure is then performed on the opposite commissural side of the valve 12. The distal end 46 of the first pair 40 of prosthetic chordae 44 that extends from the first leaflet 30 is sutured to the papillary muscle 102. Further, the distal end 48 of the second pair 42 of prosthetic chordae 44 that extends from the second leaflet 32 is also sutured to the papillary muscle 102. This suture, indicated by the reference number 112, may be a 4-0 Ethibond mattress suture with a pledget (not shown). The suture 112 extends through the distal ends 46 and 48 of both of the prosthetic chordae 44 and attaches to the papillary muscle 102 at a single location as shown in FIG. 5. Alternatively, the suture 112 may be threaded through one of the distal ends 46 and 48 of the prosthetic chordae 44 to attach it to the papillary muscle 102 at one location, and then threaded through the distal end of the other prosthetic chordae to attach it to the papillary muscle 102 at another location. It is further contemplated that a separate suture 112 could be used to attach each of the distal ends 46 and 48 of the prosthetic chordae to the papillary muscle 102.

Figure 6:
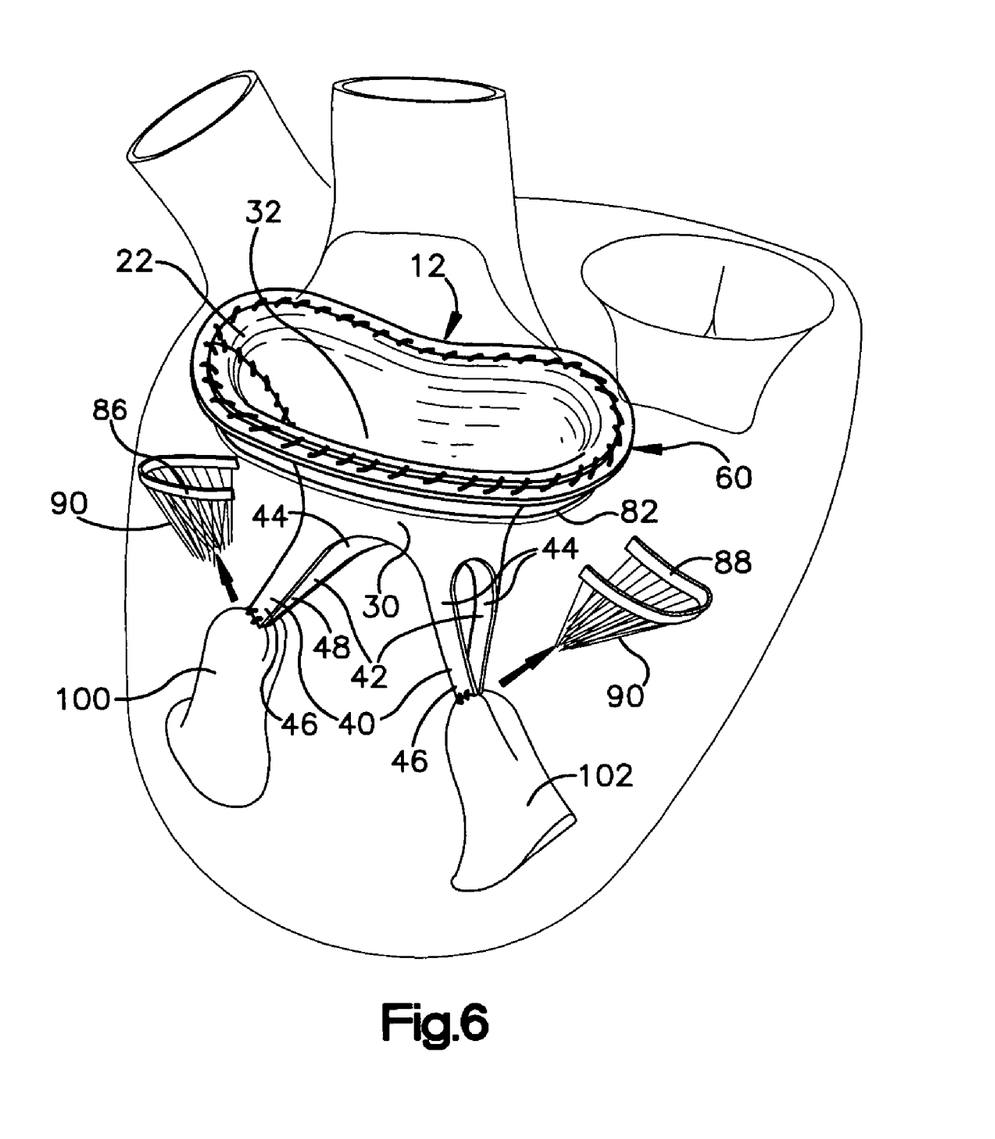
FIG. 6 is a view similar to FIG. 5 illustrating the valve at an intermediate stage of implantation in the native mitral annulus.

Following the attachment of the four prosthetic chordae 44 to the papillary muscles 100 and 102, the dissected free edges 86 and 88 of the native anterior and posterior leaflets and the native chordae tendinea 90 are then excised as shown in FIG. 6.

Figure 7:
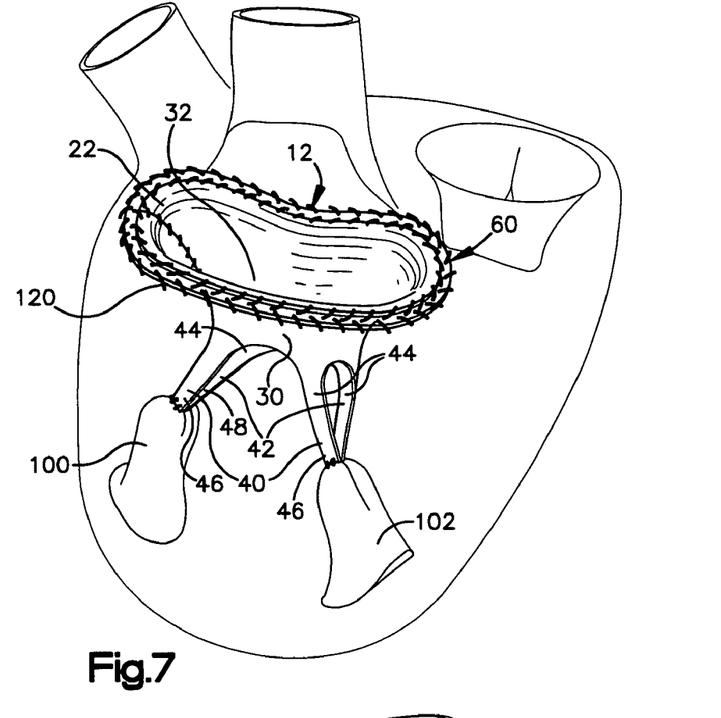
FIG. 7 is a view similar to FIG. 6 illustrating the valve at a final stage of implantation in the native mitral annulus.
Figure 8:
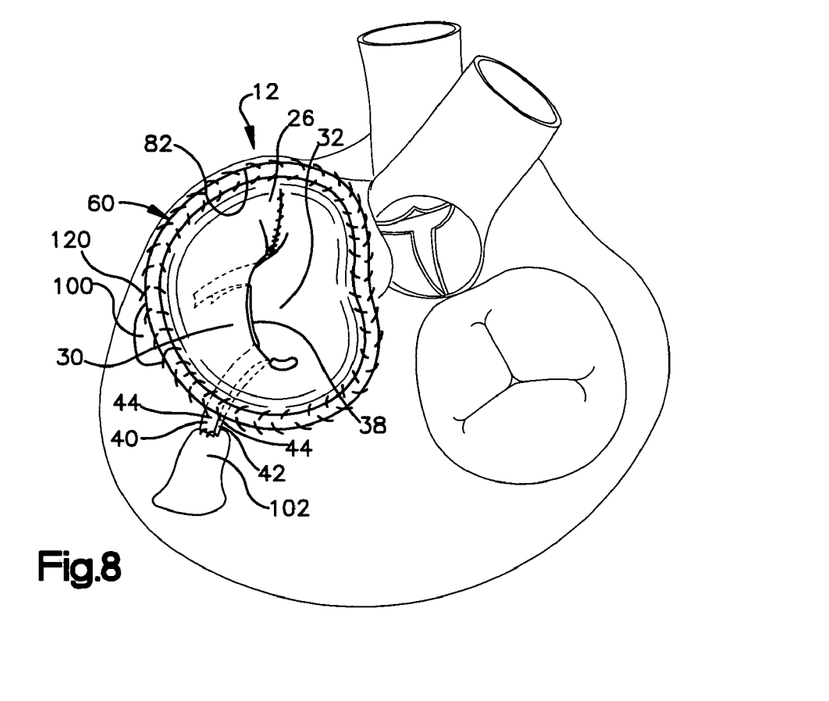
FIG. 8 is a plan view taken along line 8-8 in FIG. 7.

To complete the replacement procedure, the ring 60 at the proximal end 22 of the bioprosthetic valve 12 is sewn to the native mitral annulus 82 as shown in FIGS. 7 and 8 with sutures 120. Proper anatomical orientation of the valve 12 in the valve annulus 82 is aided by the four stay-sutures that were placed on the annulus of both mitral commissures and on the centers of the anterior and posterior leaflets 34 and 36. The sutures 120 may be three 4-0 Prolene running sutures or other suitable means. Once it is sutured to the valve annulus 82, the ring 60 functions to impede dilatation of the valve annulus and preserve the motion of the valve annulus.

The prosthetic valve 12 and associated method for replacing the native mitral valve 14 described above are useful in treating degenerative myxomatous valve with chordal rupture and annular dilatation, rheumatic valve disease, degenerative calcific mitral valve stenosis, infected mitral valve endocarditis and unsuccessful mitral valve repair.

With the distal ends 46 and 48 of the prosthetic chordae 44 being sutured to the papillary muscles 100 and 102, the prosthetic chordae are able to provide prolapse prevention and left ventricular muscle support functions. Significantly, the bioprosthetic valve 12 and the method for implanting the bioprosthetic valve described herein accomplish the goal of maintaining the continuity between the valve annulus 82 and the papillary muscles 100 and 102.

Additional benefits of the bioprosthetic valve 12 and associated method for implanting include:

A) a large orifice with an adequate circumference correlated with the size of the patient's body surface area, unrestrictive to a central free flow, compatible with high cardiac output at exercise, a low pressure required to open the valve, and without an increased gradient across the valve;

B) rapid opening and closure at all pressure ranges, without regurgitate flow and obstruction of the left ventricle outflow tract;

C) no rigid support or stent in the mitral area to allow the physiologic contraction of the left ventricular posterior wall around the mitral annulus during systole, flexible to adapt precisely to the mitral annulus reducing the tissue stress and allowing a uniform distribution of stress on the prosthetic valve which provides longer life and a higher resistance to wear, tear, and calcification; and F) anticoagulation treatment is not required and no trauma of the blood elements is produced.

From the above description of the invention, those skilled in the art will perceive improvements, changes and modifications. Such improvements, changes and modifications within the skill of the art are intended to be covered by the appended claims.

Having described the invention, we claim:

1. A stentless bioprosthetic valve for replacing a native mitral valve resected from a valve annulus in a heart, the native mitral valve having anterior and posterior leaflets and associated native chordae tendinea, said bioprosthetic valve comprising:

at least one piece of biocompatible material comprising a bi-leaflet conduit having dimensions that correspond to the dimensions of the native mitral valve, said conduit having a proximal end and a distal end, said proximal end of said conduit defining a first annulus for suturing to the valve annulus in the heart;

said conduit including first and second leaflets that mimic the three-dimensional anatomical shape of the anterior and posterior leaflets of the native mitral valve, said first and second leaflets extending between said proximal end and said distal end of said conduit, said distal end of said conduit defining a second annulus at which said first and second leaflets terminate;

said conduit further including first and second pairs of prosthetic chordae projecting from said first and second leaflets at said second annulus, each of said prosthetic chordae comprising a solid uninterrupted extension of said at least one piece of biocompatible material, said first and second pairs of prosthetic chordae providing prolapse prevention for the bioprosthetic valve and supporting the left ventricular muscle throughout the cardiac cycle;

one of said first pair of prosthetic chordae extending from said first leaflet and having a terminal end for suturing to one of the two papillary muscles and the other of said first pair of prosthetic chordae extending from said first leaflet and having a terminal end for suturing to the other of the two papillary muscles;

one of said second pair of prosthetic chordae extending from said second leaflet and having a distal end for suturing to one of the two papillary muscles and the other of said second pair of prosthetic chordae extending from said second leaflet and having a distal end for suturing to the other of the two papillary muscles;

each of said prosthetic chordae having a proximal end extending from said second annulus, each of said prosthetic chordae having a substantially constant cross-sectional shape along an entire length of said prosthetic chordae from said proximal end to said terminal end that is sutured to the respective papillary muscle.

2. The bioprosthetic valve of claim 1 wherein said at least one piece of biocompatible material comprises harvested biological tissue.

3. The bioprosthetic valve of claim 2 wherein said harvested biological tissue comprises pericardial tissue.

4. The bioprosthetic valve of claim 1 wherein said at least one piece of biocompatible material comprises an artificial tissue.

5. The bioprosthetic valve of claim 1 further comprising a biocompatible, unstented ring connected to said first annulus for supporting said first annulus and for suturing to the valve annulus in the heart, said ring, when sutured to the valve annulus, impeding dilatation of the valve annulus and preserving motion of the valve annulus.

6. The bioprosthetic valve of claim 5 wherein said ring is formed from said at least one piece of biocompatible material that has been folded over itself and sutured at the proximal end of said conduit.

7. The bioprosthetic valve of claim 5 wherein said ring is a separate piece of biocompatible material that is sutured about said first annulus.

8. The bioprosthetic valve of claim 7 wherein said ring comprises a synthetic material.

9. The bioprosthetic valve of claim 7 wherein said ring comprises harvested biological tissue.

10. The bioprosthetic valve of claim 7 wherein said ring extends radially outwardly of a peripheral edge of said first annulus.

11. The bioprosthetic valve of claim 7 wherein said ring is wrapped around a peripheral edge of said first annulus.

* * * * *